US00PP29912P3

(12) United States Plant Patent
Hansen

(10) Patent No.: US PP29,912 P3
(45) Date of Patent: Nov. 27, 2018

(54) ***PHLOX* PLANT NAMED 'FASHIONABLY EARLY LAVENDER ICE'**

(50) Latin Name: ***Phlox* hybrid**
Varietal Denomination: Fashionably Early Lavender Ice

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 68 days.

(21) Appl. No.: 15/530,084

(22) Filed: Dec. 1, 2016

(65) Prior Publication Data

US 2018/0160601 P1 Jun. 7, 2018

(51) Int. Cl.
*A01H 5/02* (2018.01)

(52) U.S. Cl.
USPC ..... Plt./320
CPC ..... *A01H 5/02* (2013.01)

(58) Field of Classification Search
USPC ..... Plt./320
CPC ..... A01H 5/02; A01H 5/00; A01H 6/70
See application file for complete search history.

(56) References Cited

U.S. PATENT DOCUMENTS

PP22,234 P3 * 11/2011 Bartels ..... A01H 5/02
Plt./320

OTHER PUBLICATIONS

Michell's 2015-16 Availability List Walters Gardens, Inc. retrieved on Nov. 28, 2017, retrieved from the Internet at http://www.michells.com/availabilities/Waltersavailability.pdf, pp. 1, 23 and 28. (Year: 2016).*

* cited by examiner

*Primary Examiner* — June Hwu

(57) ABSTRACT

A new and unique cultivar of garden *phlox* named *Phlox* 'Fashionably Early Lavender Ice' multi-stemmed, dense, slowly-spreading habit with bright-green, glossy, thick-substance, lanceolate leaves. Flowers beginning very early summer, continuing for about five weeks and repeating through mid-fall are sweetly-fragrant, producing sweetly-fragrant, initially very light lavender flower faces becoming near white with light purple eye zones. Foliage stays clean and resists mildew.

1 Drawing Sheet

Botanical classification: *Phlox* hybrid.
Variety denomination: 'Fashionably Early Lavender Ice'.

BACKGROUND OF THE INVENTION

The present invention relates to a new and distinct cultivar of *Phlox* plant, known as *Phlox* 'Fashionably Early Lavender Ice' and will be referred to hereafter by its cultivar name, 'Fashionably Early Lavender Ice', or the "new plant". The new plant was the result of a single seedling selection from the cross of *Phlox* 'Barsixtytwo' U.S. Plant Pat. No. 22,234 times *Phlox* 'Minnie Pearl' (not patented) performed at a wholesale perennial nursery in Zeeland, Mich. in the summer of 2012. The new plant was originally given the breeder code 12-53-01 after passing the initial evaluation in the summer of 2013. 'Fashionably Early Lavender Ice' has been asexually propagated by stem cuttings in the greenhouses at the same nursery in Zeeland, Mich. The unique characteristics of the new plant have been found to be reproducible and stable in successive generations of asexually propagated plants, and the resultant plants have been found to be identical to the original selection.

No plants of *Phlox* 'Fashionably Early Lavender Ice' have been sold, in this country or anywhere in the world, prior to the filing of this application, nor has any disclosure of the new plant been made prior to the filing of this application with the exception of that which may have been disclosed within one year of the filing date of this application and was either derived directly or indirectly from the inventor.

BRIEF SUMMARY OF THE PLANT

*Phlox* 'Fashionably Early Lavender Ice' is unique from its parents and all other tall garden *phlox* or other *Phlox* known to the inventor. The new plant differs from the female parent *Phlox* 'Barsixytwo' by having light lavender flowers with a tiny light purple eye compared to the coral red of 'Barsixytwo', and the new plant also has shiny foliage. Compared to the male parent 'Minnie Pearl' the new plant is earlier flowering, producing light lavender flowers rather than the white flowers of 'Minnie Pearl'. The nearest comparison variety is the co-pending 'Amethyst Pearl' U.S. Plant Pat. No. 28,487. 'Amethyst Pearl' has a deeper lavender flower than the new plant, which is a light lavender flower. 'Fashionably Early Lavender Ice' differs from all other *phlox* known to the inventor in the following repeatedly observed traits in combination:

1. Plants of dense habit, slowly spreading by short rhizomes, producing clean, glossy, bright-green, lanceolate leaves.
2. Foliage thicker substance than *Phlox paniculata* types showing exceptional powdery mildew resistance.
3. Multiple stems produce rounded heads of flowers very early in the season.

4. Sweetly fragrant flowers of light lavender on strong flexible stems of about 72 to 80 cm tall.
5. Excellent re-blooming through mid-fall when deadheaded.

BRIEF DESCRIPTION OF THE DRAWINGS

The photographs of the new plant demonstrate the unique traits of 'Fashionably Early Lavender Ice' and the overall appearance of the plant at two-years-old. The colors are as accurate as reasonably possible with color reproductions. Variation in ambient light spectrum, source and direction may cause the appearance of minor variation in color.

DETAILED BOTANICAL DESCRIPTION

Figure 1:
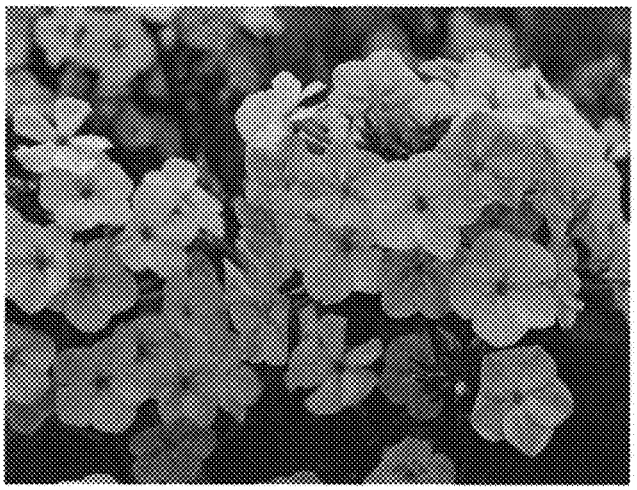
FIG. 1 shows a close-up of the floriferous flower head with flowers and buds; lighter flowers being more mature and faded and darker lavender flowers being more freshly opened.
Figure 2:
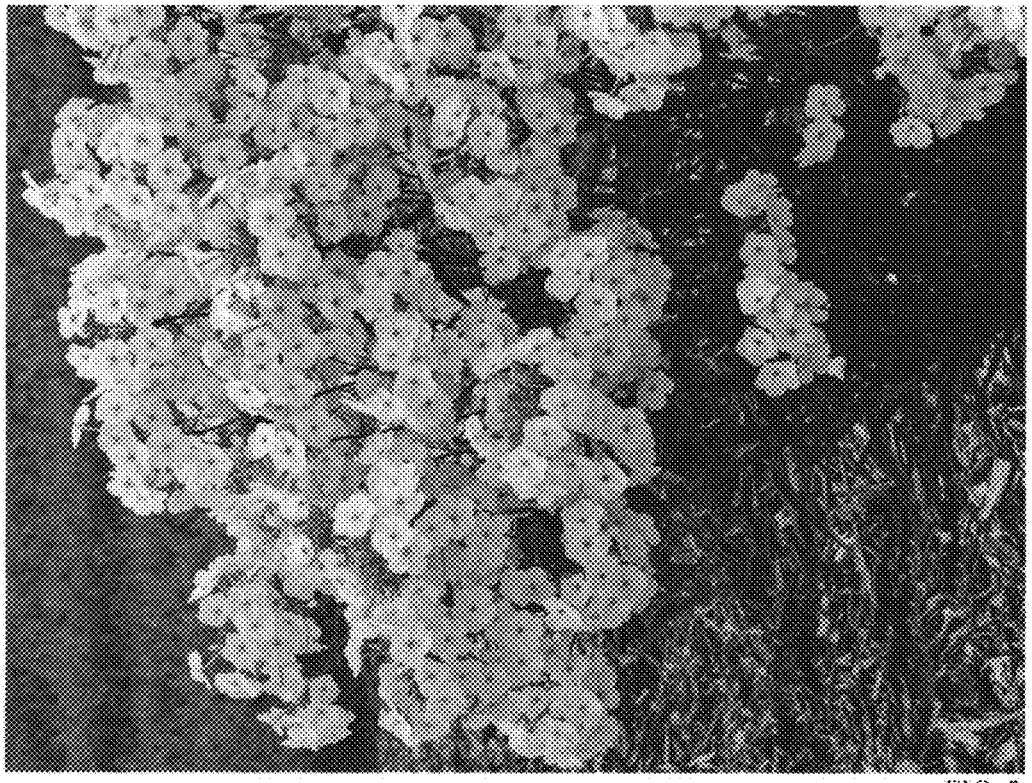
FIG. 2 shows the new plant in flower in the landscape with late spring to early summer foliage.

The following descriptions and color references are based on the 2001 edition of The Royal Horticultural Society Colour Chart except where common dictionary terms are used. *Phlox* 'Fashionably Early Lavender Ice' has not been observed under all possible environments. The phenotype may vary slightly with different growing environments such as temperature, light, fertility, soil pH, moisture and maturity levels, but without any change in the genotype. The following observations and size descriptions are based on two-year-old plants in the full sun trial garden of a wholesale perennial nursery in Zeeland, Mich. with supplemental fertilizer and water as needed.

Botanical classification: *Phlox* hybrid;

Parentage: female or seed parent *Phlox* 'Barsixtytwo' U.S. Plant Pat. No. 22,234; male or pollen parent *Phlox* 'Minnie Pearl' (not patented);

Plant habit: Hardy herbaceous perennial, densely upright, producing about 20 rigid upright stems; about 72 to 80 cm tall at flowering and about 84.0 cm wide at flowers; flowering begins late spring in Michigan continuing for about 5 weeks and repeating through mid-fall or until heavy frost if deadheaded;

Propagation: Stem cuttings; rooting in about 14 days;

Time to produce finished crop in 3.8 liter pots: About 8 to 10 weeks; moderate rate of growth;

Root: primary roots to about 1.0 mm thick; secondary fibrous and freely branching; color creamy white to tan depending on soil type glabrous abaxial; puberulent near adaxial vein; lustrous adaxial, matte abaxial; acute apex, rounded base; to about 15.5 cm long by about 1.9 cm wide, average about 12.5 cm long by about 1.8 cm wide;

Leaf color at flowering: Abaxial between RHS 146B and RHS 146C; adaxial nearest RHS 141A;

Foliage fragrance: None detected;

Veins: Reticulate; glabrous abaxial, puberulent adaxial; midvein about 1.0 mm wide at base, slightly sunken adaxial and costate abaxial;

Vein color: Abaxial midrib nearest RHS 146A, adaxial midrib between RHS N144A and RHS 146D; other adaxial and abaxial veins same color as surrounding tissue;

Petiole: Short, about 2.0 mm long and 4.0 mm across;

Petiole color: Nearest RHS 146A abaxial and between RHS N144A and RHS 146D adaxial;

Stems: Terete; stiff; strong; upright; sparsely puberulent; about 20 stems per plant; average about 70.0 cm long and 3.5 mm diameter at base;

Stem color: Between RHS 145A and RHS 146D with light speckling of nearest RHS 187B;

Nodes: About 10 per stem below flowers; average internode length about 7.0 cm; shorter proximally and longer distally;

Node color: Between RHS 145A and RHS 146D;

Flowers: Perfect; rotate, salverform, actinomorphic; typically with five petals; about 2.8 cm long total with tube about 2.5 cm long; face about 2.8 cm across; held in a branched compound corymb of about 50 to 70 flowers; attitude upright to outward;

Flower longevity: About 5 days on plant or as cut flower; self-cleaning;

Flower fragrance: Pleasantly sweet;

Buds one to two days prior to opening: Narrowly oblanceolate, to nearly clavate; acute apex with petals twisted about each other; about 2.6 cm long and 2.5 mm diameter in tube and swollen to 3.8 mm diameter toward apex;

Bud color: Tube base nearest 150D, tube center between RHS N82A and RHS N82B; swollen apex nearest RHS 85C;

Petals: Five, glabrous except pubescent for about 4.0 mm to 6.5 mm from base of adaxial or inner tube; margin entire; apex rounded; basal 2.5 cm fused into tube, face to about 2.5 cm across; adaxial about 10.0 mm of tube throat, rounded limbs with rounded apex; limbs about 1.4 cm across, imbricate about 2.5 mm of the petals to either side;

Young petal color: Abaxial or outer tube base nearest RHS 150D, abaxial tube middle between RHS 77A and RHS 77B; abaxial distal perimeter face nearest RHS N82D, surrounding corolla tube near white, lighter than RHS 85D or more white than RHS 155D; adaxial throat radiating star nearest RHS N78D gradually lightening toward apex, adaxial tube base nearest RHS 155D and middle tube nearest RHS N82A;

Mature petal color before dehiscence: Adaxial face radiating star nearest RHS 72D, remaining face near white, nearest RHS 155D; abaxial tube middle nearest RHS 82C;

Androecium: Typically five;

*Filaments.*—Five, fused to inner petals except free in terminal 1.0 mm; varying lengths between 15.0 mm and 20.0 mm above base, less than 0.2 mm in diameter; color white, lighter than RHS 155D.

*Anther.*—Five; oblong elliptic; dorsifixed; longitudinal; joined at different heights about 2.0 mm 2.3 mm and 2.5 mm above base; about 2.0 mm long by 0.5 mm wide; color nearest RHS 13B.

*Pollen.*—Nearly microscopic; abundant; spherical; color nearest RHS 17B.

Gynoecium: One pistil per flower;

*Style.*—Terete; about 2.1 cm long and 0.3 mm diameter when flower is mature; color nearest RHS 145C.

*Stigma.*—Trifurcate in the distal 2 mm, less than 0.25 mm in diameter; persistent after flower abscission; nearest RHS 6B.

*Ovary.*—Superior; elliptic with slight acute apex; about 2.0 mm long and 1.0 mm diameter; color nearest RHS 145A.

Sepals: Five, glabrous; lanceolate; sharply acute apex, margin entire; individually about 9.5 mm long and 1.0 mm wide; fused in basal 7.0 mm forming tube 2.5 mm diameter at base and 3.5 mm diameter at apex;

Sepal color: Abaxial apical 0.5 mm nearest RHS 187A, midsection nearest RHS 138B to RHS N186D in high light exposure, margins (about 0.2 mm wide) translucent with some pigment nearest RHS 187D; adaxial apex nearest RHS 187A, center nearest RHS 138B with slight blush tinting nearest RHS 187B, margins (about 0.5 mm wide) translucent with some blush nearest RHS 187D;

Peduncle: Minutely puberulent, stiff, strong, upright, terete; about 2.0 mm diameter at base of main stem and 1.0 mm diameter of branches; flowering portion about 10.0 cm long with flowers spreading 12.0 cm across the inflorescence;

Peduncle color: Between RHS 145A and RHS 146D with heavy speckling nearest RHS 187B on areas of heavy light exposure;

Fruit and seeds have not been observed;

Hardiness and culture: The new plant grows best with plenty of moisture and adequate drainage; hardy to at least from USDA zone 4 through 8.

Disease and pest resistance: *Phlox* 'Fashionably Early Lavender Ice' demonstrated the excellent powdery mildew resistance under conditions that would normally show symptoms.

It is claimed:

1. A new and distinct cultivar of hybrid *phlox* plant named *Phlox* 'Fashionably Early Lavender Ice', as herein described and illustrated.

* * * * *